United States Patent [19]

McGee et al.

[11] Patent Number: 4,763,071

[45] Date of Patent: Aug. 9, 1988

[54] NONDESTRUCTIVE TEST INSTRUMENT FOR DETERMINING FIBER VOLUME, PLY COUNT AND THICKNESS OF FIBER-CONTAINING ELECTRICALLY CONDUCTIVE COMPOSITE MATERIALS

[75] Inventors: Allen C. McGee, Fremont; Everett L. Solen, Los Gatos, both of Calif.

[73] Assignee: Lockheed Missiles & Space Company, Inc., Sunnyvale, Calif.

[21] Appl. No.: 52,193

[22] Filed: May 20, 1987

Related U.S. Application Data

[63] Continuation of Ser. No. 796,377, Nov. 8, 1985, abandoned.

[51] Int. Cl.4 ............... G01N 27/72; G01R 33/12; G01B 7/10
[52] U.S. Cl. ............... 324/233; 324/229; 324/236
[58] Field of Search ............... 324/202, 229, 230, 233, 324/DIG. 1, 227, 234, 236

[56] References Cited

U.S. PATENT DOCUMENTS

| | | | |
|---|---|---|---|
| 2,162,009 | 6/1939 | Goldsmith, Jr. | 324/234 |
| 2,764,734 | 4/1956 | Yates | 324/229 |
| 3,159,784 | 12/1964 | Haslett et al. | 324/233 |

*Primary Examiner*—Reinhard J. Eisenzopf
*Assistant Examiner*—Walter E. Snow
*Attorney, Agent, or Firm*—John J. Morrissey

[57] ABSTRACT

A probe (10) inductively couples radio-frequency electromagnetic energy into a test piece that is made of a multi-ply graphite-epoxy composite material whose fiber volume, ply count and/or thickness are to be measured. The probe (10) and the test piece form a system characterized by an electrical impedance vector, whose magnitude and phase are determined by the composition of the test piece. A frequency synthesizer (16) drives a compensating circuit (15), which applies the output of the frequency synthesizer (16) to the probe (10). The waveform and frequency of the frequency synthesizer (16) are selected to optimize the amount of energy coupled from the probe (10) into the test piece. A measurement of voltage at point A in one leg of the compensating circuit (15), and a measurement of phase difference between point A in one leg and point B in the other leg of the compensating circuit (15), are converted to a resistance measurement (corresponding to the real component of the impedance) and a reactance measurement (corresponding to the imaginary component of the impedance) of the system. The resistance and reactance measurements are plotted as coordinates on a rectangular Cartesian coordinate system. A templet comprising resistance and reactance coordinates for reference pieces whose fiber volume, ply count and thickness are known is superimposed on the same coordinate system, and lines are drawn connecting the coordinates for reference pieces of constant ply count. The position of the resistance and reactance coordinates for a test piece along a line connecting the resistance and reactance coordinates for two reference pieces indicates the fiber volume, ply count and thickness of the test piece.

7 Claims, 2 Drawing Sheets

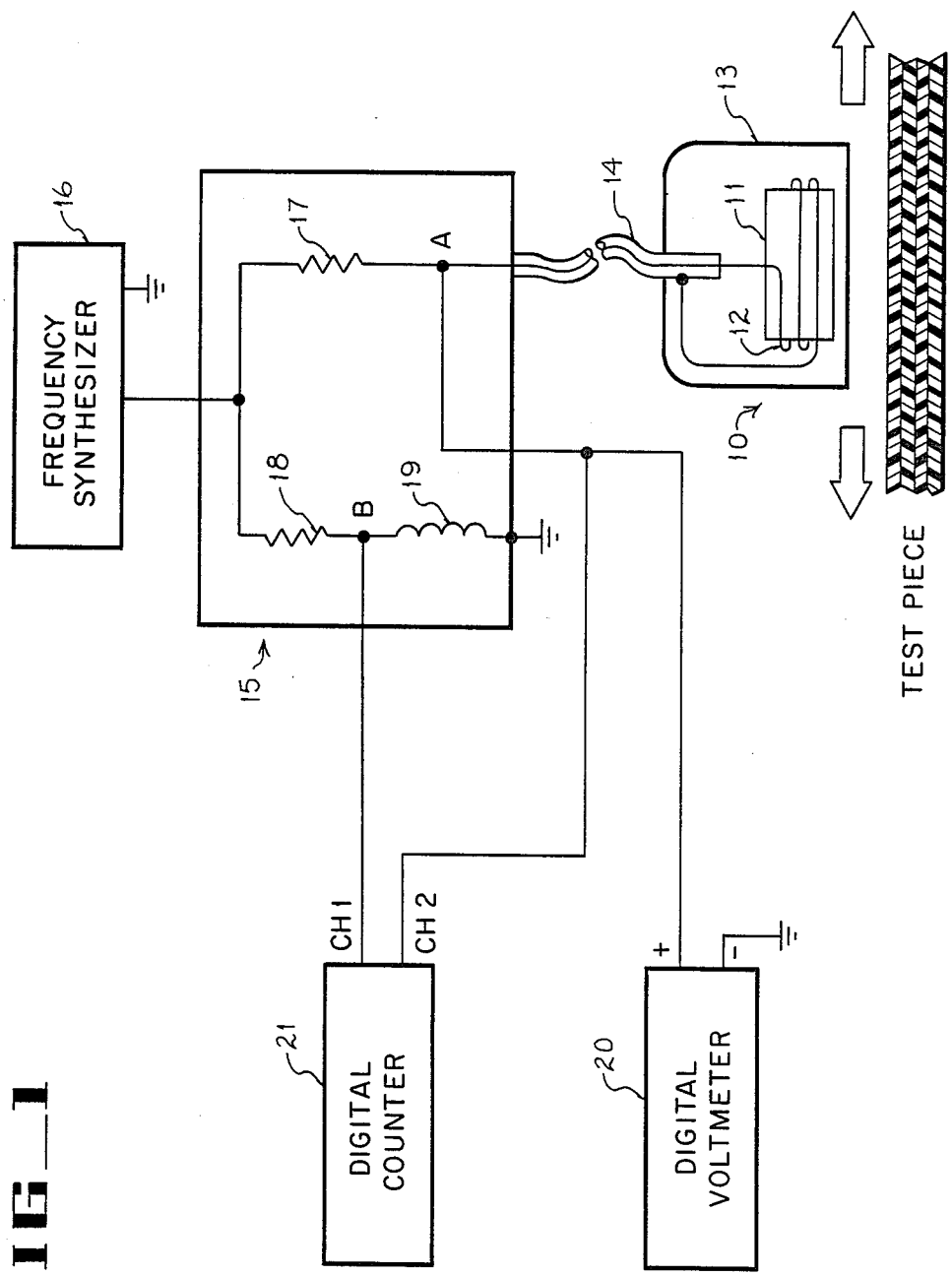
FIG_1

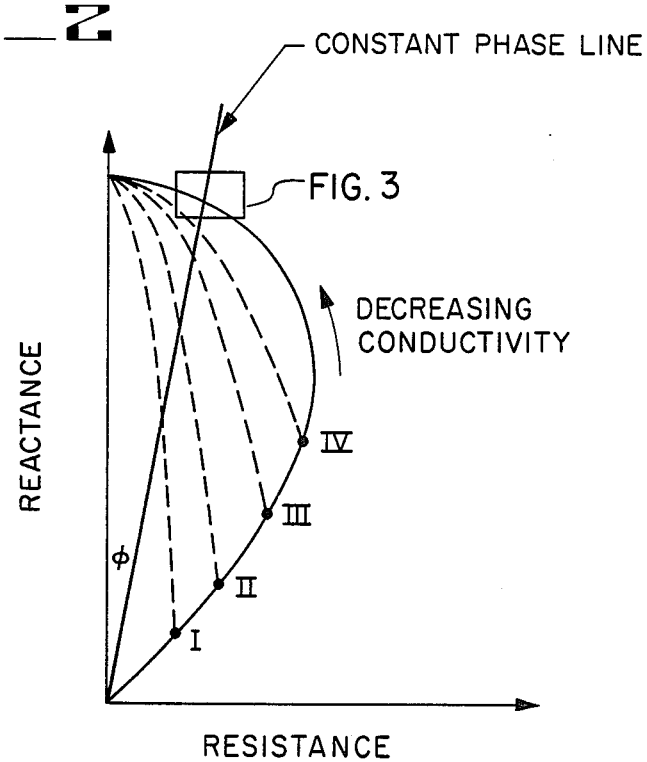
FIG_2
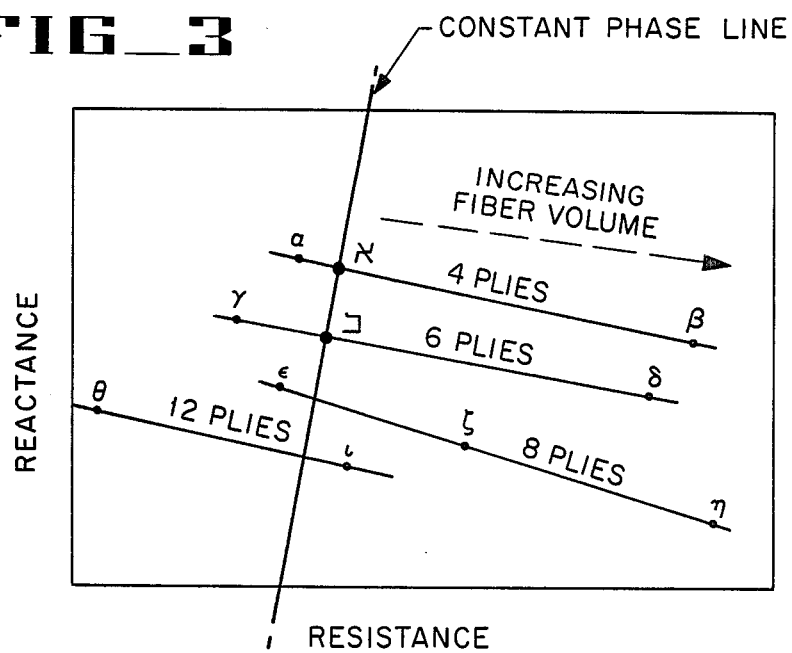
FIG_3

NONDESTRUCTIVE TEST INSTRUMENT FOR DETERMINING FIBER VOLUME, PLY COUNT AND THICKNESS OF FIBER-CONTAINING ELECTRICALLY CONDUCTIVE COMPOSITE MATERIALS

This application is a continuation of application Ser. No. 06/796,377, filed Nov. 8, 1985, and now abandoned.

TECHNICAL FIELD

This invention relates generally to nondestructive testing, and more particularly to an eddy current technique for nondestructively determining fiber volume, ply count and thickness of graphite-epoxy composite materials.

BACKGROUND ART

The most commonly used technique at the present time for determining fiber volume for graphite-epoxy composite materials is the acid digestive method, which is described in reference manual ANSI/ASTM-D-3171-76 published by the American Society for Testing Materials. The acid digestive method is an inherently destructive testing method.

Ply count for a graphite-epoxy composite material is generally determined at the present time by sectioning of the composite material. Sectioning is, of course, an inherently destructive testing method.

Pulsed eddy current techniques for nondestructive testing are discussed in texts such as:

a. Introduction to Electromagnetic Nondestructive Test Methods by H. L. Libby, published by R. E. Krieger Publishing Co. (1979), pages 122–177 and 258–268; and b. Nondestructive Testing by W. J. McGonnagle, published by Gordon and Breach (1977), pages 382–385.

However, until the present invention, no eddy current technique had been developed that was capable of uniquely determining fiber volume, ply count or thickness of any fiber-containing composite material.

SUMMARY OF THE INVENTION

The present invention provides a method and apparatus for nondestructively determining fiber volume, ply count and thickness of fiber-containing composite materials such as graphite-epoxy composites.

In particular, the present invention provides a method and apparatus for nondestructively determining fiber volume, ply count and thickness of a test piece comprising a fiber-containing composite material in real time by a technique that requires access to only one side of the test piece.

In accordance with the present invention, a probe for inductively coupling electromagnetic energy into an electrically conductive test piece is positioned adjacent the test piece to form a system characterized by an impedance vector having a voltage component and a current component. A means is provided for controlling relative motion between the probe and the test piece. Electronic circuitry (including a digital counting means) detects and measures changes in the phase and magnitude of voltage and/or current components of the impedance of the system as the probe moves relative to the test piece. A change in the phase or magnitude of the voltage or current components of the impedance indicates a corresponding change in the fiber volume, ply count and/or thickness of the test piece.

DESCRIPTION OF THE DRAWING

FIG. 1 is a schematic representation of an eddy current nondestructive test instrument according to the present invention.

FIG. 2 is a generalized plot of resistance versus reactance for a system comprising a test piece and the probe of the instrument of FIG. 1 for a selected waveform and frequency of the output of the frequency synthesizer.

FIG. 3 is a graphical representation indicating relationships between changes in the resistance and/or the reactance of the system comprising the test piece and the probe of the instrument of FIG. 1 and corresponding changes in the fiber volume, ply count and/or thickness of the test piece.

BEST MODE OF CARRYING OUT THE INVENTION

A nondestructive test instrument according to the present invention, as illustrated in FIG. 1, comprises a probe 10 for inductively coupling radio-frequency electromagnetic energy into an electrically conductive test piece. The probe 10 could be, e.g., a probe of the type marketed by VM Products, Inc. of Tacoma, Wash., under the catalog No. VM101B.

The probe 10 comprises a ferrite core 11 around which an electrically conductive coil 12 is wound. The core 11 and the coil 12 are enclosed within an electrically nonconductive housing 13, which is preferably made of a durable plastic material. One end of the coil 12 is electrically connected by means of a coaxial cable 14 to a compensating circuit 15. The other end of the coil 15 is electrically grounded.

When an alternating electric current flows through the coil 12, a magnetic flux is generated. The probe 10 is positioned adjacent an electrically conductive test piece, as indicated in cross section in FIG. 1, so that the magnetic flux enters the test piece and thereby generates eddy currents therein. The test piece and the probe 10 form a system that is characterized by an electrical impedance vector. For a particular position of the probe 10 relative to the test piece, the impedance vector has a magnitude and a phase that are determined by the composition of the test piece. A change in fiber volume, ply count or thickness of the test piece causes some change in either the magnitude or the phase, or both, of the impedance vector.

A particular application of the instrument of the present invention is to determine fiber volume, ply count and/or thickness of a test piece made of a graphite-epoxy composite material. In operation, the probe 10 and the test piece are disposed with respect to each other so as to facilitate relative motion therebetween as indicated schematically by the arrows in FIG. 1. Only one side of the test piece needs to be accessed by the probe 10.

As shown in FIG. 1, the compensating circuit 15 is electrically driven by a frequency synthesizer 16, which may be a conventional device such as the synthesizer/-function generator Model No. 3325A marketed by Hewlett-Packard Company of Palo Alto, Calif. The frequency synthesizer 16 generates an output signal of a selected waveform and frequency, which drives the compensating circuit 15. The waveform and frequency of the output signal from the frequency synthesizer 16 are selected so as to optimize the amount of energy coupled from the probe 10 into the test piece.

The compensating circuit 15 comprises two RL legs in parallel, viz., a first leg (having a resistor 17) connected to the coaxial cable 14, and a second leg (having a resistor 18 and an inductor 19) that is substantially electrically equivalent to the first leg. The magnitude and the phase of the impedance vector characterizing the system formed by the probe 10 and the test piece are obtained by measuring the voltage at point A in the first leg, and by measuring the phase difference of the waveform between point A in the first leg and point B in the second leg of the compensating circuit 15, where points A and B are indicated schematically in FIG. 1. Point A is a convenient contact point between the probe 10 and the resistor 17. Point B is a convenient contact point between the resistor 18 and the inductor 19.

The voltage at point A can be measured by means of a digital voltmeter 20, which may be a conventional device such as the digital voltmeter Model No. 3455A marketed by Hewlett-Packard Company. The phase difference between points A and B in the compensating circuit 15 can be measured by means of a digital counter 21, which may be a conventional device such as the universal counter Model No. 5316A marketed by Hewlett-Packard Company. The digital counter 21 measures the time difference between points A and B for the particular waveform of the output signal generated by the frequency synthesizer 16. The inverse of the time-difference measurement so obtained gives the phase difference measurement.

The waveform of the output signal generated by the frequency synthesizer 16 could be, e.g., a train of pulses or a sine wave. If a train of pulses is used, a greater degree of accuracy in phase measurement could be obtained by connecting the output terminal of the frequency synthesizer 16 directly to the digital counter 21. If a sine wave is used, the frequency synthesizer 16 would be connected as shown in FIG. 1, in which case the phase measurement would be less accurate but could be made more quickly than by using a train of pulses.

The electrical impedance of the system illustrated in FIG. 1 can be expressed mathematically as a complex function having a real component and an imaginary component, where the real component is related to the energy dissipated from the system by eddy currents set up in the test piece, and where the imaginary component is related to the energy stored in the system. For a given geometrical disposition of the probe 10 relative to the test piece, and for a given frequency of the output signal generated by the frequency synthesizer 16, the measured values of voltage and phase obtained by the technique described above in connection with FIG. 1 can be converted to a resistance measurement (corresponding to the real component of the impedance) and a reactance measurement (corresponding to the imaginary component of the impedance). A discussion of the relationship between resistance and reactance for electrically conductive materials is found in texts such as, e.g., *Nondestructive Testing* by W. J. McGonnagle, op. cit., page 349.

It is instructive to plot the resistance and reactance materials, as obtained by the above-described technique. Thus, in FIG. 2 a generalized plot in rectangular Cartesian coordinates is provided to illustrate the relationship between resistance and reactance for electrically conductive test pieces made of various different kinds of materials, where the test pieces all have the same geometrical disposition with respect to the probe 10 for a specified waveform and frequency generated by the frequency synthesizer 16.

The solid-line curve in FIG. 2 is a fitted-curve envelope of the coordinates on a rectangular Cartesian coordinate system of resistance and reactance (illustrated as abscissa and ordinate, respectively) for different electrically conductive materials formed into test pieces of substantially identical geometrical configuration and dimensions, which are tested under substantially identical conditions. The broken-line curves in FIG. 2 are called "lift-off" curves for the particular materials I, II, III and IV. Each "lift-off" curve illustrates the change in resistance with respect to reactance as the radio-frequency energy being coupled into the test piece made of the corresponding material I, II, III or IV is removed, or (stated in another way) as the probe 10 is "lifted off" the test piece. A so-called "constant phase line" indicating a particular phase angle $\phi$ is shown by a solid straight line in FIG. 2. Since conductivity $\sigma$ is the reciprocal of resistivity, the direction indicating decreasing conductivity along the fitted curve of FIG. 2 is as shown by the small arrow adjacent the curve.

The portion of the fitted curve of FIG. 2 indicating the relationship between resistance and reactance for certain low-conductivity materials, e.g., graphite-epoxy composite materials, is enclosed within a rectangular box in FIG. 2. The portion of the fitted curve within the boxed area in FIG. 2 is seen to be approximately linear. An expanded view of the boxed area of FIG. 2 is present in FIG. 3 in which the points $\alpha, \beta, \gamma, \delta, \epsilon, \zeta, \eta, \theta$ and $\iota$ represents the coordinates of nine different graphite-epoxy composite materials. (The fitted curve of FIG. 2 is not shown in FIG. 3. However, the relevant portion of the "constant phase line" of FIG. 2 is shown in FIG. 3.)

The nine different graphite-epoxy composite materials represented by the points $\alpha, \ldots, \iota$ in FIG. 3 are reference materials whose fiber volume, ply count and thickness are accurately known from other test procedures. Thus, the material represented by the point $\alpha$ is a known 4-ply graphite-epoxy composite specimen of 58.4 mils thickness, which has a graphite fiber volume of 60% as determined by an acid digestive (i.e., a very accurate, but inherently destructive) procedure. Similarly, the other materials graphically represented in FIG. 3 have known values for fiber volume, ply count and thickness, as indicated in the following table:

| Specimen | Fiber Volume | Ply Count | Ply Thickness (mils/ply) |
|---|---|---|---|
| $\alpha$ | 60% | 4 | 14.6 |
| $\beta$ | 61% | 4 | 14.4 |
| $\gamma$ | 58% | 6 | 14.7 |
| $\delta$ | 60% | 6 | 14.3 |
| $\epsilon$ | 58% | 8 | 14.6 |
| $\zeta$ | 59% | 8 | 14.3 |
| $\eta$ | 61% | 8 | 14.0 |
| $\theta$ | 58% | 12 | 14.5 |
| $\iota$ | 59% | 12 | 14.3 |

The nine specimens listed in the table above were analyzed by the nondestructive test procedure of the present invention using an apparatus as described above in connection with FIG. 1. The voltage and phase measurements obtained using the apparatus of FIG. 1 were converted to resistance and reactance measurements using conventional mathematical relationships. The resistance and reactance measurements were then plotted as the points $\alpha, \ldots, \iota$ with the coordinates shown graphically in FIG. 3.

A straight line is shown in FIG. 3 connecting the points $\alpha$ and $\beta$ representing the 4-ply specimens. Similarly, a straight line is drawn through the points $\gamma$ and $\delta$ representing the 6-ply specimens; a straight line is drawn (or substantially fitted) through the points $\epsilon$, $\zeta$ and $\eta$ representing the 8-ply specimens; and a straight line is drawn through the points $\theta$ and $\iota$ representing the 12-ply specimens. The points $\alpha, \ldots, \iota$ on FIG. 3, and the lines on FIG. 3 connecting points representing materials having the same number of plies, serve as a templet for use in determining fiber volume, ply count and/or thickness of test pieces of unknown fiber volume, ply count and/or thickness. A change in the number of plies causes an apparent "lift-off" from the fitted curve of FIG. 2, while a change in the fiber volume for a constant number of plies causes an apparent change in conductivity along the fitted curve.

In operation, an instrument according to the present invention is used to obtain and phase measurements for a number of different reference pieces whose fiber volume, ply count and thickness measurements are already known by conventional test procedures. The voltage and phase measurements are converted to resistance and reactance measurements by well-known mathematical techniques, and a plot (which functions as a templet) such as that shown in FIG. 3 is obtained. Then, voltage and phase measurements are obtained for test pieces whose fiber volume, ply count and/or thickness are to be determined. The voltage and phase measurements for the test pieces are converted to resistance and reactance coordinates, which are plotted on the templet. In general, from the position on the templet of the point representing the resistance and reactance coordinates of any particular test piece, it is possible to obtain a quantitative indication of fiber volume, ply count and thickness of the particular test piece.

The use of an instrument according to the present invention calibrated to provide the templet of FIG. 3 enables a quantitative indication of fiber volume, ply count and thickness for test pieces made of graphite-epoxy composite materials to be obtained. A graphite-epoxy composite material whose resistance and reactance coordinates define a point that falls on the line $\alpha-\beta$ of the templet has four plies; a material whose resistance and reactance coordinates define a point that falls on the line $\gamma-\delta$ of the templet has six plies; etc. Fiber volume for a four-ply material can be determined by linear extrapolation from the resistance and reactance coordinates of the material to the known values of the coordinates of $\alpha$ and/or $\beta$ along the $\alpha-\beta$ line. Similarly, fiber volume for a six-ply material can be determined by linear extrapolation along the $\gamma-\delta$ line, and so forth for higher-number ply materials.

As is apparent from FIG. 3, a technique that measures only the phase shift as energy being is coupled into a test piece cannot uniquely distinguish among the various possible combinations of fiber volume, ply count and thickness. For a given phase angle $\phi$ as indicated by the "constant phase line" in FIGS. 2 and 3, a technique that measures only phase shift could not distinguish a test piece having four plies and a fiber volume indicated by point $\mathcal{H}$ on the $\alpha-\beta$ line from a test piece having six plies and a fiber volume indicated by point $\mathrel{\unicode{x2ea}}$ on the $\gamma-\delta$ line, where $\mathrel{\unicode{x2ea}}$ is the point of intersection of the "constant phase line" with the 4-ply $\alpha-\beta$ line, and where $\mathcal{H}$ is the point of intersection of the "constant phase line" with the 6-ply $\gamma-\delta$ line. In general, no single measurement can uniquely determine the fiber volume or the number of plies in a test piece made of a graphite-epoxy composite material. The eddy current technique of the present invention uses two simultaneous measurements (viz., a voltage measurement and a phase measurement) to distinguish various conditons of fiber volume, ply count and thickness.

The eddy current nondestructive test technique described herein can be used to obtain quantitative measurements of fiber volume, ply count and thickness for structures such as aircraft components made of graphite-epoxy composite materials. Operators acquiring skill in the technique can also estimate void content (i.e., microbubbles per unit volume) can discern delaminations in such graphite-epoxy composite structures.

A particular embodiment of a pulsed eddy current nondestructive test instrument in accordance with the present invention has been described above in connection with the determination of fiber volume, ply count and thickness of a fiber-epoxy composite material. However, other embodiments of the invention that are more particularly suitable for other applications would become apparent to workers skilled in the art upon perusal of the foregoing specification and accompanying drawing. The description of the instrument and test procedure presented above is to be considered as illustrative of the invention, which is more generally defined by the following claims and their equivalents.

We claim:

1. An instrument for nondestructively measuring a mechanical property of an electrically conductive test structure, said test structure comprising different materials having correspondingly different values of electrical conductivity, at least one of said materials having a non-zero value of electrical conductivity, measurement of said mechanical property being obtainable by specification of two electrical parameters for said test structure, said electrical parameters being variable in value independently of each other with respect to variations in said mechanical property of said test structure, said instrument comprising:

a. means for coupling electromagnetic energy into said test structure, said energy coupling means and said test structure thereby forming a system that is characterized by an impedance vector having a current component and a voltage component, said current and voltage components of said impedance vector determining said electrical parameters for said test structure;

b. means for making a magnitude measurement of one of said current and voltage components of said impedance vector, and thereby determining a corresponding magnitude measurement of the other of said current and voltage components;

c. means for measuring a phase relationship between said current and voltage components of said impedance vector simultaneously with the making of said magnitude measurement of said one of said current and voltage components, said means for measuring said phase relationship being independent of said means for making said magnitude measurement of said one of said current and voltage components, said magnitude measurement of said one of said current and voltage components together with the simultaneous measurement of said phase relationship between said current and voltage components thereby specifying values for said two electrical parameters; and d. means defining a coordinate system in which said values specified for said two electrical parameters for said test structure are coordinates of a test point representing said test structure, said means defining said coordinate system also relating said test point to a plurality of reference points representing a corresponding plurality of other electrically conductive structures, each one of said reference points having a corresponding pair of coordinates that are known values of said two electrical parameters for a corresponding one of said other electrically conductive structures, said mechanical property having a known measurement for each one of said other electrically conductive structures, the relating of said test point to said reference points thereby providing a measured value of said mechanical property for said test structure.

2. The instrument of claim 1 wherein said energy coupling means comprising a source of radio-frequency energy and an inductively coupling device.

3. The instrument of claim 1 wherein said means for making said magnitude measurements of said current and voltage components of said impedance vector, and for simultaneously measuring said phase relationship between said current and voltage components, comprises a digital voltmeter and a digital counter.

4. The instrument of claim 1 wherein said means defining said coordinate system comprises a templet on which said reference points are inscribed, said templet being disposed so that said test point appears graphically on said coordinate system in relation to said reference points when said instrument is in operation.

5. An instrument for nondestructively measuring strength of an electrically conductive test structure made of a fiber-containing material, the strength of said test structure being a function of fiber volume and thickness of said material, the strength of said test structure being specified in terms of two electrical parameters for said test structure, said electrical parameters being variable in value independently of each other with respect to variations in the fiber volume and thickness of said material, said instrument comprising:

a. means for coupling radio-frequency electromagnetic energy into said test structure, said energy coupling means and said test structure thereby forming a system characterized by an impedance vector having a current component and a voltage component, said current and voltage components of said impedance vector determining said electrical parameters for said test structure;

b. means for making a magnitude measurement of one of said current and voltage components of said impedance vector, and thereby determining a corresponding magnitude measurement of the other of said current and voltage components;

c. means for measuring a phase relationship between said current and voltage components of said impedance vector simultaneously with the making of said magnitude measurement of said one of said current and voltage components, said means for measuring said phase relationship being independent of said means for making said magnitude measurement of said one of said current and voltage components, said magnitude measurement of said one of said current and voltage components together with the simultaneous measurement of said phase relationship between said current and voltage components thereby specifying values for said two electrical parameters in terms of which the strength of said test structure is specified; and d. means defining a coordinate system in which said values specified for said two electrical parameters for said test structure are coordinates of a test point representing said test structure, said means defining said coordinate system also relating said test point to a plurality of reference points representing a corresponding plurality of other electrically conductive structures made of said fiber-containing material having different fiber volumes and thicknesses, each one of said reference points having a corresponding pair of coordinates that are known values of said two electrical parameters for a corresponding one of said other electrically conductive structures, the strength of each one of said other electrically conductive structures having a known measurement, the relating of said test point of said reference points thereby providing a measured value of the strength of said test structure.

6. The instrument of claim 5 wherein said means defining said coordinate system comprising a templet on which said reference points are inscribed, said templet being disposed so that said test point appears graphically on said coordinate system in relation to said reference points when said instrument is in operation.

7. A method for nondestructively measuring ply count, fiber volume and thickness properties of a miltiply graphite-epoxy composite structure, where said properties can be specified in terms of two electrical parameters for said composite structure, said electrical parameters being variable in value independently of each other with respect to variations in ply count, fiber volume and thickness of each composite structure, said method comprising:

a. positioning a radio-frequency energy coupling device adjacent said composite structure so that said energy coupling device and composite structure form a system characterized by an impedance vector having a current component and a voltage component, said current and voltage components of said impedance vector determining said electrical parameters for said composite structure;

b. making a magnitude measurement of one of said current and voltage components of said impedance vector, and thereby determining a corresponding magnitude measurement of the other of said current and voltage components;

c. measuring a phase relationship between said current and voltage components of said impedance vector simultaneously with the making of said magnitude measurement of said one of said current and voltage components, the measuring of said phase relationship being performed independently of the making of said magnitude measurement of said one of said current and voltage components, said magnitude measurement of said one of said current voltage components together with said simultaneous measurement components thereby specifying values for said two electrical parameters for said composite structure; and d. generating a coordinate system in which said values specified for said two electrical parameters for said composite structure are coordinates of a test point representing said composite structure, and relating said test point to a plurality of reference points representing a corresponding plurality of other multi-ply graphite-epoxy composite structures having different ply count, fiber volume and thickness properties, each one of said reference points having a corresponding pair of coordinates that are known values of said two electrical parameters for a corresponding one of said other composite structures, said properties of each one of said other composite structures having a known measurement in said coordinate system, the relating of said test point to said reference points thereby providing a measured value of said properties of said composite structure.

* * * * *